(12) United States Patent
Bhoyar et al.

(10) Patent No.: US 10,081,036 B2
(45) Date of Patent: Sep. 25, 2018

(54) METHODS AND SYSTEMS FOR LIQUID PARTICLE PREQUALIFICATION

(71) Applicant: APPLIED MATERIALS, INC., Santa Clara, CA (US)

(72) Inventors: Sankesha Bhoyar, Bhandara (IN); Mahesh Arcot, Maharashtra (IN); Nilesh Chimanrao Bagul, Bangalore (IN); Hemantha Raju, Bangalore (IN); Ravindra Patil, Thane (IN)

(73) Assignee: APPLIED MATERIALS, INC., Santa Clara, CA (US)

( * ) Notice: Subject to any disclaimer, the term of this patent is extended or adjusted under 35 U.S.C. 154(b) by 0 days.

(21) Appl. No.: 15/269,324

(22) Filed: Sep. 19, 2016

(65) Prior Publication Data

US 2018/0078975 A1 Mar. 22, 2018

(51) Int. Cl.
*B08B 3/12* (2006.01)
*B08B 3/14* (2006.01)
*G01N 15/14* (2006.01)
*G01N 15/06* (2006.01)
*C02F 1/00* (2006.01)
(Continued)

(52) U.S. Cl.
CPC ............... *B08B 3/12* (2013.01); *B08B 3/14* (2013.01); *C02F 1/001* (2013.01); *C02F 1/42* (2013.01); *G01N 15/0618* (2013.01); *G01N 15/1436* (2013.01); *C02F 2103/346* (2013.01); *C02F 2209/40* (2013.01); *C02F 2301/046* (2013.01); *G01N 2015/0693* (2013.01); *G01N 2015/1486* (2013.01)

(58) Field of Classification Search
None
See application file for complete search history.

(56) References Cited

U.S. PATENT DOCUMENTS

| 2003/0034046 A1 | 2/2003 | Guldi et al. |
| 2003/0159713 A1 | 8/2003 | Park et al. |
| 2012/0216833 A1 | 8/2012 | Wang et al. |

OTHER PUBLICATIONS

Kondo, et al., "Latest Technology and Standardization Trends for Liquid-borne Particle Counters," Bunseki, vol. 9, 2012, 11 pages.
(Continued)

*Primary Examiner* — Rita P Adhlakha
(74) *Attorney, Agent, or Firm* — Kilpatrick Townsend & Stockton LLP

(57) ABSTRACT

Systems for prequalifying components for a processing chamber are described. The systems may be used to clean particulates from chamber parts and concurrently quantify the cleanliness. The systems may be used to qualify replacement parts before sending to a customer site for installation. The systems have three adjacent compartments separated by impermeable barriers. All three compartments are filled with liquid while cleaning a chamber component. The center compartment contains a submerged component for cleaning and qualifying. Two compartments on either side of the center compartment are configured with submerged ultrasonic transducers to deliver ultrasonic energy to either side of the component being cleaned and prequalified. A liquid pump is connected to the cleaning tub to recirculate water from the cleaning bath and another liquid pump is configured to remove a small amount of the cleaning bath to sample particulates.

9 Claims, 7 Drawing Sheets

(51) Int. Cl.
*C02F 1/42* (2006.01)
*C02F 103/34* (2006.01)

(56) References Cited

OTHER PUBLICATIONS

Kondo, et al., "Measurement and Control of Liquid-borne Particles in the Semiconductor Manufacturing Process," Cleaning Technology, 2014, 11 pages.

METHODS AND SYSTEMS FOR LIQUID PARTICLE PREQUALIFICATION

FIELD

Embodiments described herein relate to determining cleanliness of manufacturing equipment and subcomponents.

BACKGROUND

In semiconductor substrate processing, the trend towards increasingly smaller feature sizes and line-widths has placed a premium on the ability to mask, etch, and deposit material on a semiconductor substrate with greater precision. As semiconductor features shrink, device structures become more fragile. Meanwhile, the killer defect size, defined as the particle size which renders the device non-functional, becomes smaller and more difficult to remove from the surface. Consequently, reducing device damage is one of the major drivers in the development of cleaning processes. As a result, this trend towards increasingly smaller feature sizes has placed a premium on the cleanliness of semiconductor manufacturing processes including the chamber component parts used in such processes.

Cleaning processes may be performed on chamber subcomponents and replacement parts either at the customer site or at the primary semiconductor manufacturing facility. Determining the cleanliness of the subcomponents and replacement parts may be performed as a separate operation prior to installation. The determination of cleanliness may involve cleaning and qualification performed in separate equipment or even separate facilities. This often undesirably involves transferring the article from a cleaning tool into a separate analysis tool. The sample may even be transferred to a separate facility or a separate company to perform analysis involved in qualification.

There is a need for an improved apparatus and process for cleaning chamber component parts that provide improved removal of particle contaminants from chamber parts while significantly reducing any delay until the chamber part is qualified for end-use.

SUMMARY

Systems for prequalifying components for a processing chamber are described. The systems may be used to clean particulates from chamber parts and concurrently quantify the cleanliness. The systems may be used to qualify replacement parts before sending to a customer site for installation. The systems have three adjacent compartments separated by impermeable barriers. All three compartments are filled with liquid while cleaning a chamber component. The center compartment contains a submerged component for cleaning and qualifying. Two compartments on either side of the center compartment are configured with submerged ultrasonic transducers to deliver ultrasonic energy to either side of the component being cleaned and prequalified. A liquid pump is connected to the cleaning tub to recirculate water from the cleaning bath and another liquid pump is configured to remove a small amount of the cleaning bath to sample particulates.

Embodiments disclosed herein include an ultrasonic cleaning and sampling system. The systems include a cleaning tub. The systems further include a first ultrasonic tub and a second ultrasonic tub. The first ultrasonic tub is disposed on the opposite side of the cleaning tub from the second ultrasonic tub. The systems further include a first impermeable barrier disposed between the first ultrasonic tub and the cleaning tub. The first impermeable barrier is configured to pass ultrasonic energy from the first ultrasonic tub into the cleaning tub when each of the first ultrasonic tub and the cleaning tub are filled with water. The systems further include a second impermeable barrier disposed between the second ultrasonic tub and the cleaning tub. The second impermeable barrier is configured to pass ultrasonic energy from the second ultrasonic tub into the cleaning tub when each of the second ultrasonic tub and the cleaning tub are filled with water. The systems further include a first ultrasonic transducer and a second ultrasonic transducer. The first ultrasonic transducer is in the first ultrasonic bath and the second ultrasonic transducer is in the second ultrasonic bath. The systems further include an ultrapure water source configured to deliver ultrapure water into the cleaning bath. The systems further include a sampling pump fluidly coupled to the cleaning bath and configured to remove contaminated water from the cleaning bath. The systems further include a liquid particle counter fluidly coupled to the dilution unit and configured to measure the particle concentration of the contaminated water using optical scattering. The systems further include a recirculation pump fluidly coupled to the cleaning bath. The systems further include a large particle filter fluidly coupled to the recirculation pump. The systems further include a small particle filter fluidly coupled to the large particle filter. A recirculation path is fluidly coupled to the cleaning bath at an outlet and an inlet. The recirculation path includes the recirculation pump, the large particle filter and the small particle filter.

The first ultrasonic transducer may be configured to be driven at a first frequency greater than 20 kHz to produce cavitation in the cleaning tub. The first ultrasonic transducer and the second ultrasonic transducer may be configured to be driven at a same frequency to concurrently produce cavitation in the cleaning tub. The first ultrasonic transducer may be configured to be driven at a first megasonic frequency to produce cavitation in the cleaning tub. A recirculation pumping speed of the recirculation pump may be between 10 liters/min and 200 liters/min. The first ultrasonic tub may be configured such that the first ultrasonic transducer is submersible. The small particle filter may be selected to remove particles larger than 10 nm while passing particles smaller than 10 nm. The large particle filter may be selected to remove particles larger than 30 nm while passing particles smaller than 30 nm. The recirculation path further may comprise an ion-exchange filter.

Embodiments disclosed herein include an ultrasonic cleaning and sampling system. The systems include a cleaning tub. The systems further include a first ultrasonic tub and a second ultrasonic tub. The first ultrasonic tub is disposed on the opposite side of the cleaning tub from the second ultrasonic tub. The systems further include a first impermeable barrier disposed between the first ultrasonic tub and the cleaning tub. The first impermeable barrier is configured to pass ultrasonic energy from the first ultrasonic tub into the cleaning tub when each of the first ultrasonic tub and the cleaning tub are filled with water. The systems further include a second impermeable barrier disposed between the second ultrasonic tub and the cleaning tub. The second impermeable barrier is configured to pass ultrasonic energy from the second ultrasonic tub into the cleaning tub when each of the second ultrasonic tub and the cleaning tub are filled with water. The systems further include a first ultrasonic transducer and a second ultrasonic transducer. The first ultrasonic transducer is in the first ultrasonic bath and the second ultrasonic transducer is in the second ultrasonic bath. The systems further include an ultrapure water source configured to deliver ultrapure water into the cleaning bath. The systems further include a sampling pump fluidly coupled to the cleaning bath and configured to remove contaminated water from the cleaning bath. The systems further include a dilution unit fluidly coupled to the sampling pump and configured to dilute the contaminated water by a factor of at least 500. The systems further include a liquid particle counter fluidly coupled to the dilution unit and configured to measure the particle concentration of the contaminated water using optical scattering.

A sampling pumping speed of the sampling pump may be between 0.001 milliliters/min and 10 milliliters/min. The dilution unit may be configured to dilute the contaminated water by a factor of at least 500 by adding at least 500 times more ultrapure water from the ultrapure water source. Each of the first impermeable barrier and the second impermeable barrier may be sheets of polypropylene, plastic, glass or quartz. The liquid particle counter is configured to detect particle sizes down to and including 100 nm.

Embodiments disclosed herein include methods of removing a contaminant from a surface of a part to-be-cleaned. the methods include placing the part to-be-cleaned into a cleaning tub disposed between a first ultrasonic tub and a second ultrasonic tub. The methods further include filling the cleaning tub with ultrapure water to form a cleaning bath. The methods further include filling the first ultrasonic tub and the second ultrasonic tub with water. The methods further include applying ultrasonic energy at a first frequency to a first ultrasonic transducer and at a second frequency to a second ultrasonic transducer. The first ultrasonic transducer is disposed within the first ultrasonic tub and the second ultrasonic transducer is disposed within the second ultrasonic tub. The methods further include transmitting the ultrasonic energy through the water across an impermeable barrier and into the cleaning bath. The methods further include removing the contaminant from the surface. The methods further include forming contaminated water by adding the contaminant to the cleaning bath. The methods further include flowing the contaminated water into a liquid particle counter. The methods further include determining a contamination concentration of the contaminated water in the liquid particle counter. The contamination concentration may be compared to an endpoint contamination concentration and the ultrasonic energy may be stopped if the contamination concentration is less than the endpoint contamination concentration.

To better understand the nature and advantages of the present invention, reference should be made to the following description and the accompanying figures. It is to be understood, however, that each of the figures is provided for the purpose of illustration only and is not intended as a definition of the limits of the scope of the present invention.

DESCRIPTION OF THE DRAWINGS

A further understanding of the nature and advantages of the disclosed technology may be realized by reference to the remaining portions of the specification and the drawings.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Systems for prequalifying components for a processing chamber are described. The systems may be used to clean particulates from chamber parts and concurrently quantify the cleanliness. The systems may be used to qualify replacement parts before sending to a customer site for installation. The systems have three adjacent compartments separated by impermeable barriers. All three compartments are filled with liquid while cleaning a chamber component. The center compartment contains a submerged component for cleaning and qualifying. Two compartments on either side of the center compartment are configured with submerged ultrasonic transducers to deliver ultrasonic energy to either side of the component being cleaned and prequalified. A liquid pump is connected to the cleaning tub to recirculate water from the cleaning bath and another liquid pump is configured to remove a small amount of the cleaning bath to sample particulates.

Figure 1A:
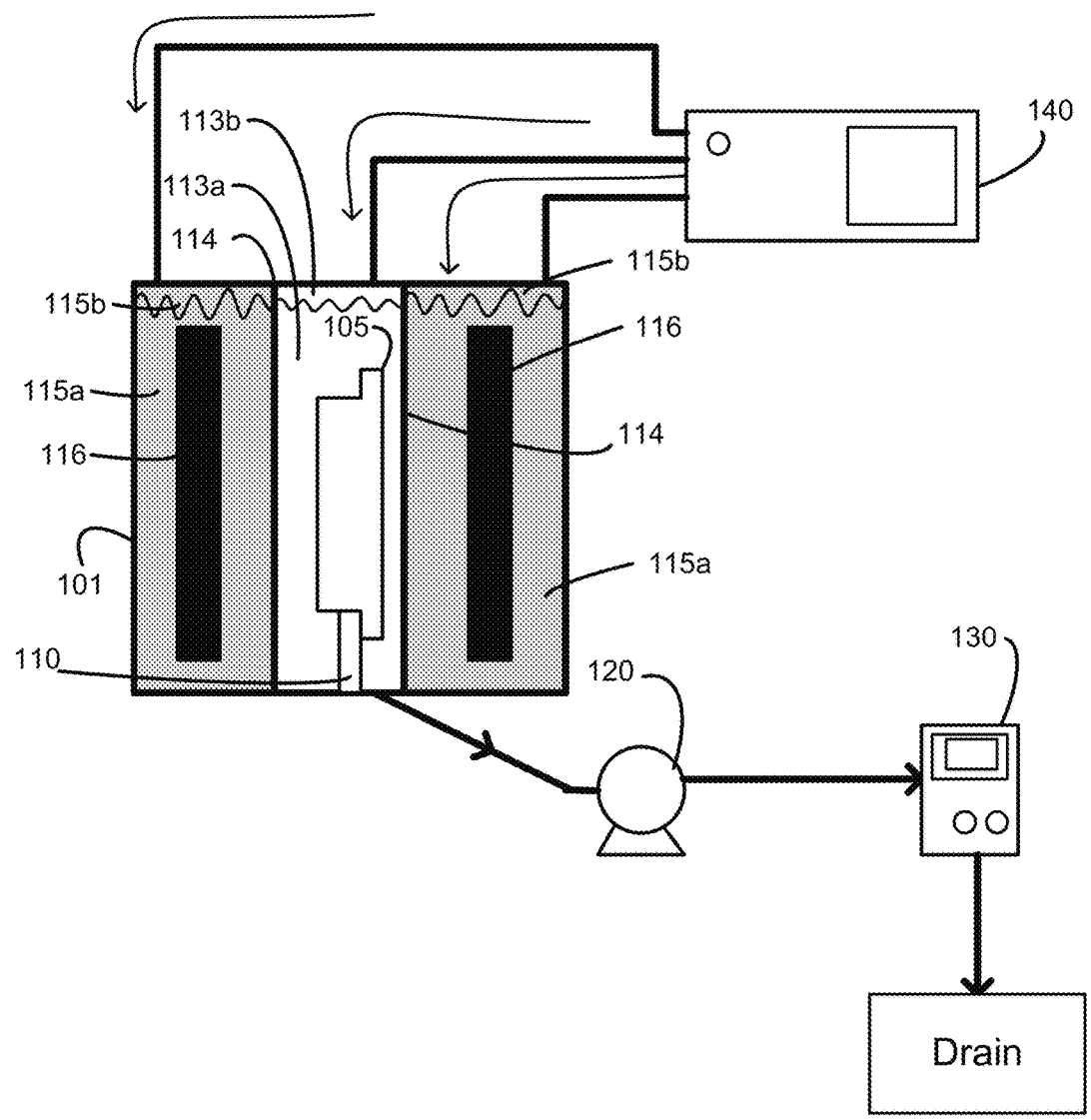
FIG. 1A shows a system for cleaning and sampling components for a substrate processing chamber according to embodiments.

FIG. 1A shows a system for cleaning and sampling components for a substrate processing chamber according to embodiments. Any or all aspects of the embodiments depicted in each of FIGS. 1A, 1B, 1C, 1D may be combined to form other embodiments. An ultrapure water (UPW) source 140 is used to supply and/or replenish water to the cleaning tub of sampling bath 101. Ultrapure water source 140 may include one, two or more filtering stages, in embodiments, and generally will also include a polishing stage typically disposed following the filtering stages. The one or more filtration stages are used to reduce particulate concentration and the polishing stage is used to reduce the concentration of ionized particulates, ionized minerals and ionized organic molecules. Ultrapure water, filtered water or unfiltered water may be used to fill or replenish each of the ultrasonic baths 115a contained in ultrasonic tubs 115b in embodiments.

Sampling bath 101 comprises three compartments separated by impermeable barriers 114. Impermeable barriers 114 do not allow water to pass through but do transmit sound waves (e.g. ultrasonic energy, megasonic energy or gigasonic energy). The center compartment is a spare part bath 113a in cleaning tub 113b which is separated from an ultrasonic bath 115a in ultrasonic tub 115b on either side by impermeable barriers 114. Impermeable barriers 114 do not allow liquid, ions or particulates to flow from spare part bath 113 to or from either of the two ultrasonic baths 115a in ultrasonic tubs 115b in embodiments. Impermeable barriers 114 impede all mass transport from either ultrasonic bath 115a into spare part bath 113a according to embodiments. Each of spare part tub 113b and ultrasonic tubs 115b are equipped with drains (not shown) for quickly removing dumping cleaning bath 113a and ultrasonic baths 115a and refilling with ultrapure water from ultrapure water source 140 described previously. Alternatively, any water may be used to (re)fill ultrasonic tubs 115b since impermeable barriers 114 will not allow particulates, ions or other contaminants to enter spare part bath 113a in cleaning tub 113b. In this description the chamber component being cleaned and qualified may be referred to as a "spare part" but, generally speaking, the chamber component may be any part intended for installation onto a substrate processing chamber especially on the interior of the chamber. The chamber component may be a refurbished part, a new spare part, an original part or any part, in embodiments, intended for use of a substrate processing chamber. Sampling bath 101 or the walls of sampling bath 101 may comprise or consist of polypropylene, polyvinylidene fluoride (PVDF), polyethylene, glass or quartz in embodiments.

Spare part bath 113a receives spare part 105 onto spare part support 110 in the center compartment located between two ultrasonic baths 115a. Ultrapure water is prepared in ultrapure water source 140 and flowed into cleaning tub 113b. The ultrapure water may sometimes be referred to as UPW in the literature and may have a resistivity of above 18.2MΩ-cm and total organic content (TOC) of below 5 ppb or between 1 and 5 ppb in embodiments. The ultrapure water may only possess particulates below 7 nm, below 5 nm or below 3 nm according to embodiments. The small size initially present in the ultrapure water facilitates the measurement of particles originating from spare part 105. Cleaning tub 113b may be filled before or after receiving spare part 105 according to embodiments. Once spare part 105 and spare part bath 113a are together, contaminants begin to detach from spare part 105 and enter spare part bath 113a. Contaminants (including particulates) may then be removed from cleaning tub 113b and spare part bath 113a by a variety of means described herein.

Contaminants may be removed from cleaning tub 113b and spare part bath 113, in part, by flowing through sampling pump 120 and a liquid particle counter 130 according to embodiments before being flowed into the drain. Sampling pump 120 may be a peristaltic pump to accurately control the flow rate and to help ensure particles detected in liquid particle counter 130 are primarily indicative of the cleanliness of spare part 105. The liquid particle counter (LPC) may be configured with an optical scattering system to detect particle sizes down to and including 30 nm, 50 nm, 80 nm and/or 100 nm. The contaminated water is the ultrapure water plus any contaminants which have been added from the part to-be-cleaned during the cleaning process. The contaminated water may be flowed into a drain after the concentration of the defects have been measured.

Sampling bath 101 further includes two ultrasonic transducers 116 one in each of the two ultrasonic baths 115a in each of the two ultrasonic tubs 115b. One ultrasonic transducer 116 (as well as one ultrasonic bath 115a/ultrasonic tub 115b) are disposed on either side of spare part bath 113. Positioning an ultrasonic transducer 116 on either side has been found to enhance the removal rate of particles from spare part 105 during cleaning and prequalification. The cavitational energy is created in each of ultrasonic bath(s) 115a and spare part bath 113a in embodiments. One or both of ultrasonic transducers 116 are excited by a frequency greater than 20 kHz, greater than 40 kHz, greater than 60 kHz, greater than 80 kHz, greater than 100 kHz, greater than 200 kHz, greater than 500 kHz or greater than 1 MHz according to embodiments. Higher frequencies have been found to correlate with reduced boundary layer and increased particle removal probabilities. Reduced boundary layer and increased particulate removal probabilities benefit the equipment and processes described herein. Typical ultrasonic transducers are operated below 50 kHz which have been found to leave some particulates on spare part 105 due to the larger boundary layer surrounding spare part 105. Megasonic frequencies are, generally, more effective at removing particulates of interest as the frequency is increased towards and above the megahertz frequency region.

Impermeable barrier 114 may be a sheet of material which does not allow liquid to diffuse from one side to the other. Impermeable barrier 114 may be a relatively thin sheet of material. Impermeable barrier 114 may be a polypropylene, plastic, glass or quartz sheet according to embodiments. Impermeable barrier 114 may have a thickness of greater than 0.5 mm, greater than 1 mm or greater than 2 mm in embodiments. Impermeable barrier 114 may have a thickness of less than 20 mm, less than 10 mm or less than 5 mm in embodiments. Other aspects of the invention will be described in the context of three further embodiments.

Figure 1B:
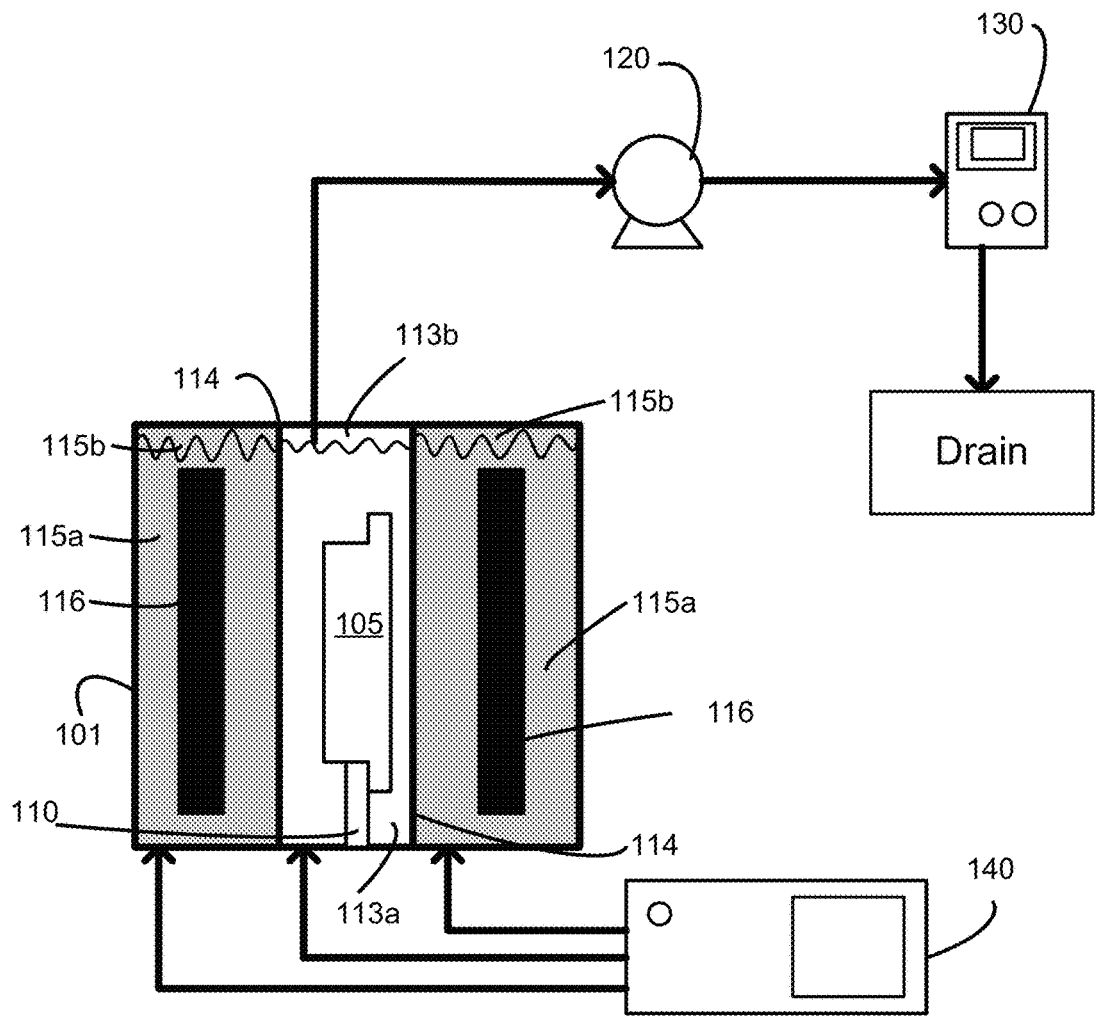
FIG. 1B shows a system for cleaning and sampling components for a substrate processing chamber according to embodiments.

FIG. 1B shows a system for cleaning and sampling components for a substrate processing chamber according to embodiments. An ultrapure water (UPW) source 140 is used to supply and replenish water to sampling bath 101. Ultrapure water source 140 may include the components described previously.

Sampling bath 101 again comprises three compartments separated by impermeable barriers 114 which inhibit the flow of water but transmit sound waves (e.g. ultrasonic energy including megasonic and gigasonic energy). Cleaning tub 113b contains spare part bath 113a and is separated from an ultrasonic tub 115b containing ultrasonic bath 115a on either side by impermeable barriers 114 having properties described earlier. Impermeable barriers 114 impede all mass transport from either ultrasonic bath 115a into spare part bath 113a in embodiments. In this description the chamber component to-be-cleaned and qualified may be a spare part, a refurbished part, an original part or any part to-be-cleaned. The part to-be-cleaned may ultimately be used in a substrate processing chamber in embodiments.

Spare part bath 113a receives spare part 105 onto spare part support 110 in the center compartment located between two ultrasonic baths 115a. Ultrapure water is prepared in ultrapure water source 140 and flowed into cleaning tub 113b to form spare part bath 113a. The ultrapure water may have a resistivity of above 18.2MΩ-cm and total organic content (TOC) of below 5 ppb or between 1 and 5 ppb in embodiments. The ultrapure water may only possess particulates below 7 nm, below 5 nm or below 3 nm according to embodiments. The small size initially present in the ultrapure water facilitates cleaning of spare part 105 and further facilitates the measurement of particles originating from spare part 105. Once spare part 105 and the ultrapure water are together, contaminants begin to depart from spare part 105 and may be removed from spare part bath 113a to quantify contamination.

Contaminants may be removed from spare part bath 113a by a tube placed near the top of the waterline where particulates may preferentially collect. The tube may be placed within 10%, within 5% or within 3% of the top of spare part bath 113a as measured relative to the mean waterline of spare part bath 113a. Contaminated water may be flowed through sampling pump 120 and a liquid particle counter 130 according to embodiments before being pumped into a drain as shown. Sampling pump 120 may be a peristaltic pump to allow accurate and selectable control of flow rate at low flow volumes. Sampling pump 120 may be selected to ensure particles detected in liquid particle counter 130 are indicative of the cleanliness of spare part 105 in embodiments. Liquid particle counter 130 may be configured with an optical scattering system to detect particle sizes down to and including 30 nm, 50 nm, 80 nm and/or 100 nm according to embodiments.

Sampling bath 101 further includes two ultrasonic transducers 116 one in each of the two ultrasonic baths 115a. The term ultrasonic may be used herein to encompass any frequency above 20 kHz and therefore includes megasonic and gigasonic frequencies. Positioning one ultrasonic transducer 116 on either side of spare part bath 113a has been found to enhance the removal rate of particles from spare part 105 during cleaning and prequalification, especially when higher frequencies (>50 kHz, megasonic and gigasonic) are used. higher frequencies benefit from line-of-sight access to contaminated portions of spare part 105. The cavitational energy is created in ultrasonic bath(s) 115a and/or spare part bath 113a, in embodiments. One or both of ultrasonic transducers 116 are excited by a frequency greater than 20 kHz, greater than 40 kHz, greater than 60 kHz, greater than 80 kHz, greater than 100 kHz, greater than 200 kHz, greater than 500 kHz or greater than 1 MHz according to embodiments. Higher cavitational frequencies correlate with a greater probability of dislodging particulates from spare part 105 over the frequencies described herein. Impermeable barrier 114 may be a sheet of material which does not allow liquid to diffuse from one side to the other. Impermeable barrier 114 may be a plastic, glass or quartz sheet, in embodiments, and may have a thickness of greater than 0.5 mm, greater than 1 mm or greater than 2 mm in embodiments. In a preferred embodiment, the plastic sheet is a polypropylene sheet.

Figure 1C:
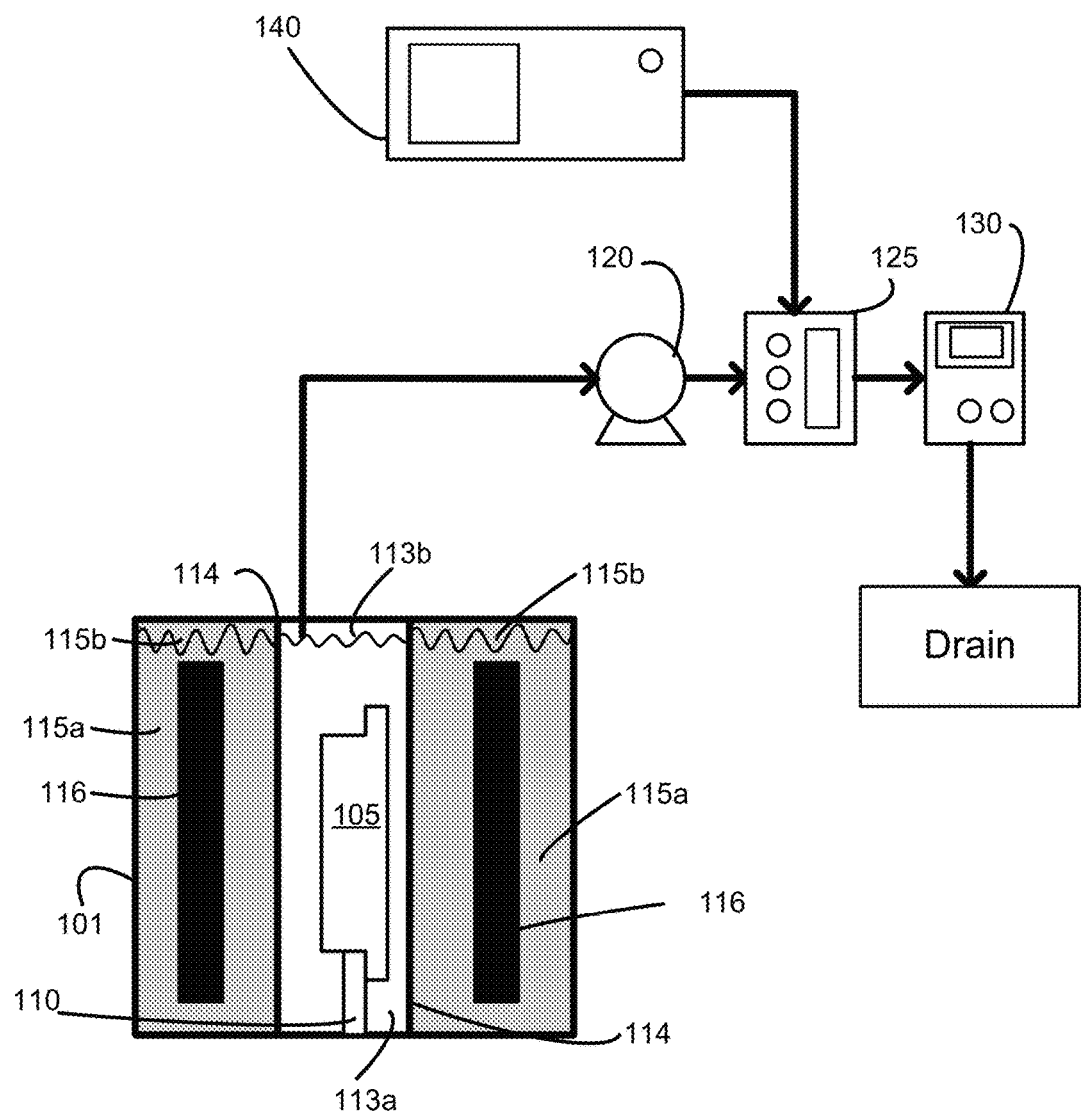
FIG. 1C shows a system for cleaning and sampling components for a substrate processing chamber according to embodiments.

FIG. 1C shows a system for cleaning and sampling components for a substrate processing chamber according to embodiments. An ultrapure water (UPW) source 140 is used to supply and/or replenish water to sampling bath 101. Ultrapure water source 140 may include one, two or more filtering stages, in embodiments, and generally will also include a polishing stage typically disposed following the filtering stages. The one or more filtration stages are used to reduce particulate concentration and the polishing stage is used to reduce the concentration of ionized particulates, ionized minerals and ionized organic molecules.

Sampling bath 101 comprises three compartments separated by impermeable barriers 114. Impermeable barriers 114 do not allow water to pass through but do transmit sound waves at least in the ultrasonic frequency range. Spare part bath 113a is separated from an ultrasonic bath 115a disposed on either side by impermeable barriers 114. Impermeable barriers 114 do not allow liquid, ions or particulates to flow from either of the two ultrasonic baths 115a to spare part bath 113a. Impermeable barriers 114 impede all mass transport from either ultrasonic bath 115a into spare part bath 113a in embodiments. In all examples described herein the chamber component being cleaned and qualified is referred to as a "spare part" but, generally speaking, the chamber component may be any part intended for installation onto a substrate processing chamber especially on the interior of the chamber.

Spare part bath 113a receives spare part 105 onto spare part support 110 in the center compartment located between two ultrasonic baths 115a as before. Ultrapure water is prepared in ultrapure water source 140 and flowed into cleaning tub 113b to form spare part bath 113a. The ultrapure water have a resistivity of above 18.2MΩ-cm and total organic content (TOC) of below 5 ppb or between 1 and 5 ppb in embodiments. The ultrapure water may only possess particulates below 7 nm, below 5 nm or below 3 nm according to embodiments. The small size initially present in the ultrapure water facilitates the measurement of particles originating from spare part 105. Once spare part 105 and the ultrapure water are together, contaminants begin to depart from spare part 105 and may be removed from spare part bath 113a.

Contaminants in the formerly ultrapure water (e.g. "contaminated water") are removed from spare part bath 113a by flowing through sampling pump 120, a dilution system 125 and a liquid particle counter 130 according to embodiments prior to being dumped into a drain. Sampling pump 120 may be a peristaltic pump to ensure a controlled reproducible low flow rate. Sampling pump 120 may be configured to control the flow rate to between 0.001 ml/min and 10 ml/min, between 0.01 ml/min and 3 ml/min or between 0.03 ml/min and 1 ml/min according to embodiments. As a consequence of the high sensitivity of some liquid particle counters 130 the water may be diluted in dilution system 125 by a factor of 500× to 10,000× with water from ultrapure water source 140. Diluting the water pumped by sampling pump 120 may reduce the chances of running into the saturation limit of liquid particle counter 130. The water may be diluted by greater than 500×, greater than 1,000×, greater than 2,000×, or greater than 3,000× according to embodiments. The liquid particle counter (LPC) may be configured with an optical scattering system to detect particle sizes down to and including 30 nm, 50 nm, 80 nm and/or 100 nm.

As before, sampling bath 101 further includes two ultrasonic transducers 116 one in each of the two ultrasonic baths 115a/ultrasonic tubs 115b. Positioning one ultrasonic transducer 116 on either side of spare part bath 113a/cleaning tub 113b has been found to enhance the removal rate of particles from spare part 105 during cleaning and prequalification. The cavitational energy may be created in spare part bath 113a in embodiments and may or may not be created in ultrasonic baths 115a due to the absence of a spare part. One or both of ultrasonic transducers 116 are excited by a frequency greater than 20 kHz, greater than 40 kHz, greater than 60 kHz, greater than 80 kHz, greater than 100 kHz, greater than 200 kHz, greater than 500 kHz or greater than 1 MHz according to embodiments. Higher frequencies beneficially reduce the boundary layer thickness and beneficially increase particle removal probabilities. Impermeable barrier 114 may be a sheet of material which does not allow liquid to diffuse from one side to the other. Other aspects of impermeable barrier 114 have been described previously.

Figure 1D:
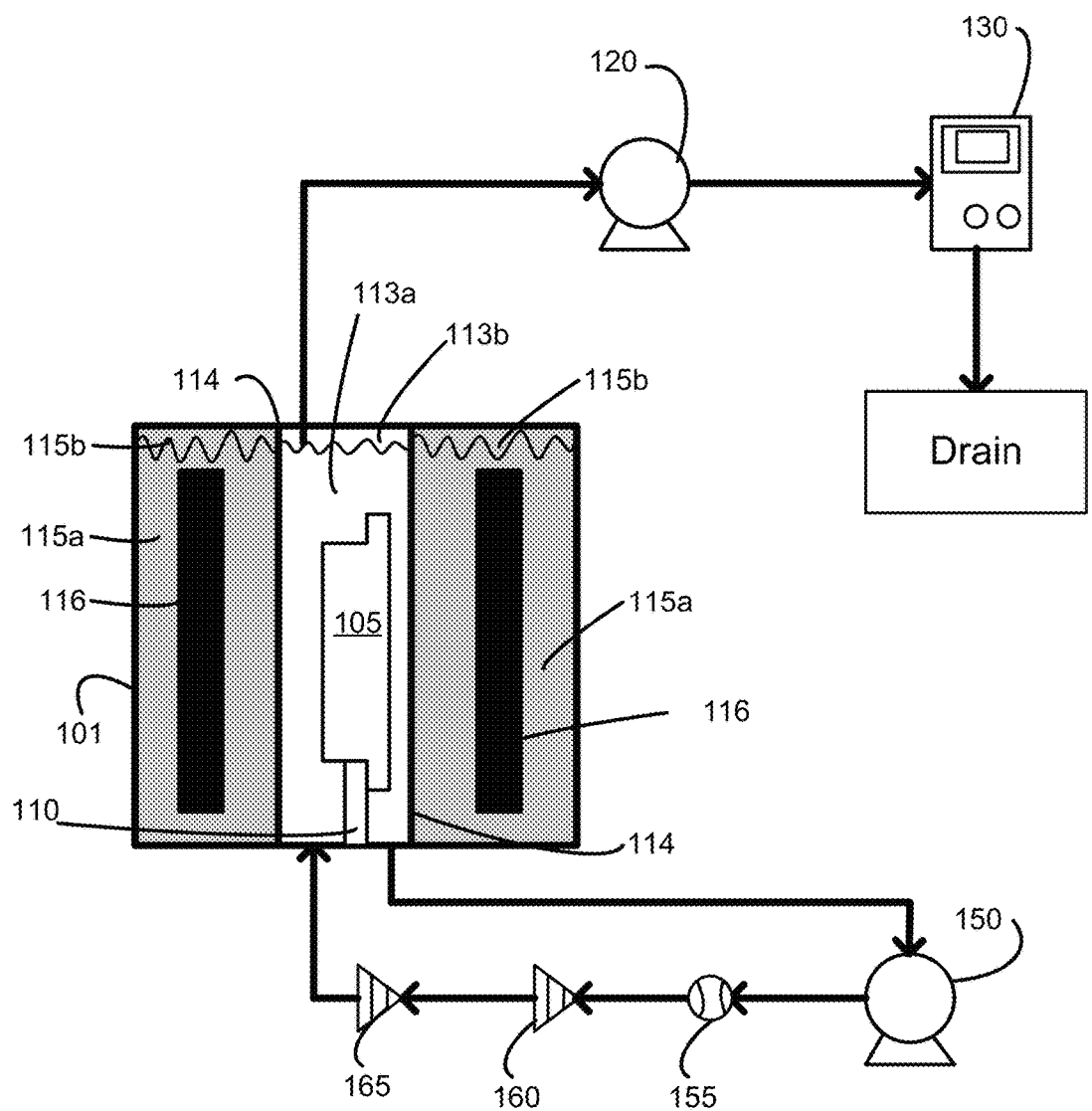
FIG. 1D shows a system for cleaning and sampling components for a substrate processing chamber according to embodiments.

FIG. 1D shows a system for cleaning and sampling components for a substrate processing chamber according to embodiments. An ultrapure water (UPW) source 140 (not shown) is used to supply and replenish water to sampling bath 101. The properties of the ultrapure water were described previously.

Sampling bath 101 comprises three compartments separated by impermeable barriers 114. Impermeable barriers 114 do not allow water to pass through but do transmit sound waves (e.g. ultrasonic energy or frequencies above 20 kHz). The center compartment is a cleaning bath 113a placed in a cleaning tub 113b. Cleaning bath 113a is separated from an ultrasonic bath 115a on either side by impermeable barriers 114. Impermeable barriers 114 do not allow liquid, ions or particulates to flow from either of the two ultrasonic baths 115a into cleaning bath 113a. Impermeable barriers 114 impede all mass transport from either ultrasonic bath 115a into cleaning bath 113a in embodiments. In this description the chamber component being cleaned and qualified may be referred to as a "spare part" or more generally a part to-be-cleaned.

Cleaning bath 113a receives spare part 105 onto spare part support 110 in the center compartment located between two ultrasonic baths 115a. Ultrapure water is prepared in ultrapure water source 140 and flowed into cleaning tub 113b to form cleaning bath 113a. The ultrapure water may only possess particulates below 7 nm, below 5 nm or below 3 nm according to embodiments. The small size initially present in the ultrapure water facilitates the measurement of particles originating from spare part 105. Cleaning tub 113b may be filled before or after receiving spare part 105 according to embodiments. Once spare part 105 and the ultrapure water are together, contaminants begin to leave surfaces of spare part 105 and may additionally be removed from cleaning bath 113a as follows.

Contaminants may be removed by recirculating the water within cleaning bath 113a. The water may be flowed through a recirculation pump 150, a flowmeter 155 (optional), a large particle filter 160 and a small particle filter 165 according to embodiments. Optional flowmeter 155 may be a non-contact flowmeter, in embodiments, to help limit the particulates in cleaning bath 113 and limit the collection of total organic content (TOC) below the upper limits or within the ranges described herein. Recirculation pump 150 may be a magnetically-coupled centrifugal pump, in embodiments, to reduce the potential for introducing defects which would be counterproductive. The water may flow through the recirculation pump 150, flowmeter 155 (optional), large particle filter 160 and small particle filter 165 in sequence according to embodiments. Flowmeter 155 may be a non-contact flowmeter to further improve cleanliness and lengthen filter lifespan in embodiments. Large particle filter 160 may actually be two or more filters connected in parallel (not shown) in embodiments. According to embodiments, small particle filter 165 may analogously be a plurality of small particle filters (not shown). The pumping speed of recirculation pump 150 may be between 10 liters/min and 200 liters/min, between 15 liters/min and 150 liters/min or between 20 liters/min and 100 liters/min in embodiments. Recirculation pump 150 may be a seal-less magnetic drive pump according to embodiments. An ion-exchange filter may also be included at any point in the recirculation path to increase the resistivity of the water back to or above 18.2MΩ-cm. The high resistivities recited herein have been found to increase the particulate cleanliness on the clean spare part 105 by preventing metal-ion contamination which serve as particulate nucleation points.

Large particle filter 160 may only allow passage for particles below 30 nm, below 20 nm or below 15 nm in embodiments. Small particle filter 165 may only allow particles smaller than 10 nm, smaller than 7 nm, smaller than 5 nm or smaller than 3 nm to pass through according to embodiments. The recited filter sizes allow the water to return to the initial particle cleanliness present in the ultrapure water (UPW) generated in the ultrapure water source 140.

An additional filter elements be included along the recirculation route to further improve the cleaning efficiency and reduce the false-count rate registered in liquid particle counter 130. Bubbles in cleaning bath 113 may be detected as particles in liquid particle counter 130 since optical scattering detection techniques may scatter light from the surface of a bubble in much the same way particle surfaces scatter the light. Smaller bubbles (e.g. <50 nm) stay resident in liquids such as cleaning bath 113 for a long time. A degasser may be included to hasten the removal of dissolved gases from cleaning bath 113 in embodiments. Degassers are available which remove up to 80% of the dissolved gases from cleaning bath 113. Reducing dissolved air in cleaning bath 113 removes a source of bubbles.

A pressurized sample collection chamber may be included in all the embodiments described herein. A small chamber continually collects water from cleaning bath 113 at a pressure higher than a cleaning pressure of cleaning bath 113. The elevated pressure in the pressurized sample collection chamber drives out bubbles prior to measuring the particulate concentration with liquid particle counter 130. The pressurized sample collection chamber may be a region within liquid particle counter 130 or may be a separate unit, according to embodiments. A debubbler may further be included along the sampling path in embodiments. A debubbler may be connected between sampling pump 120 and liquid particle counter 130 in all embodiments described herein according to embodiments.

All pumps, filters and other components in all recirculating or sampling paths described herein may be selected to change the water in less than ten minutes, less than five minutes or less than three minutes according to embodiments. The flow rate or the refilling rate may independently be greater than 10 liters/min greater than 20 liters/min or greater than 30 liters/min in embodiments. The size of cleaning tub 113b and/or cleaning bath 113a may be between 10 liters and 300 liters, between 20 liters and 200 liters or between 50 liters and 150 liters according to embodiments. The size of either or each of ultrasonic baths 115a or ultrasonic tubs 115b may be between 10 liters and 300 liters, between 20 liters and 200 liters or between 50 liters and 150 liters in embodiments.

In all embodiments described herein, an impermeable barrier 114 may be disposed between cleaning tub 113b and ultrasonic tub 115b. Impermeable barrier 114 may be in direct contact with cleaning bath 113a and ultrasonic bath 115a in embodiments. The other borders of cleaning bath 113a and ultrasonic bath 115a may be in contact with more substantial materials which do not need to pass ultrasonic energy. The walls of sampling bath 101 may comprise polypropylene, polyvinylidene fluoride, glass or quartz. Put another way, ultrasonic tub 115b may comprise polypropylene, polyvinylidene fluoride, glass or quartz in embodiments. Similarly, cleaning tub 113b may comprise polypropylene, polyvinylidene fluoride, glass or quartz according to embodiments.

Contaminants may also depart from cleaning bath 113a by flowing through sampling pump 120, a dilution system 125 (optional) and a liquid particle counter 130 according to embodiments prior to being flowed into the drain. Sampling pump 120 may be a peristaltic pump to ensure a controllable low flow rate and to ensure that particles detected in liquid particle counter 130 are primarily indicative of the cleanliness of spare part 105. The liquid particle counter (LPC) may be configured with an optical scattering system to detect particle sizes down to and including 30 nm, 50 nm, 80 nm and/or 100 nm.

Sampling bath 101 may further include two ultrasonic transducers 116 one in each of the two ultrasonic baths 115. Positioning one ultrasonic transducer 116 on either side of cleaning bath 113a/cleaning tub 113b has been found to enhance the removal rate of particles from spare part 105 during cleaning and prequalification in embodiments. The cavitational energy is created in each of ultrasonic bath(s) 115a and cleaning bath 113a in embodiments. One or both of ultrasonic transducers 116 are excited by a frequency greater than 20 kHz, greater than 40 kHz, greater than 60 kHz, greater than 80 kHz, greater than 100 kHz, greater than 200 kHz, greater than 500 kHz or greater than 1 MHz according to embodiments. Higher frequencies correlate with reduced boundary layer and increased particle removal probabilities, each of which benefit the equipment and processes described herein. Typical ultrasonic transducers are operated below 50 kHz which has been found to leave some particulates on spare part 105 due to the significant boundary layer surrounding spare part 105. Megasonic frequencies are typically above 350 kHz and are progressively more effective at removing particulates of interest as the frequency is increased into the (~MHz) frequency region and beyond. Impermeable barrier 114 may have the properties described previously.

Figure 2:
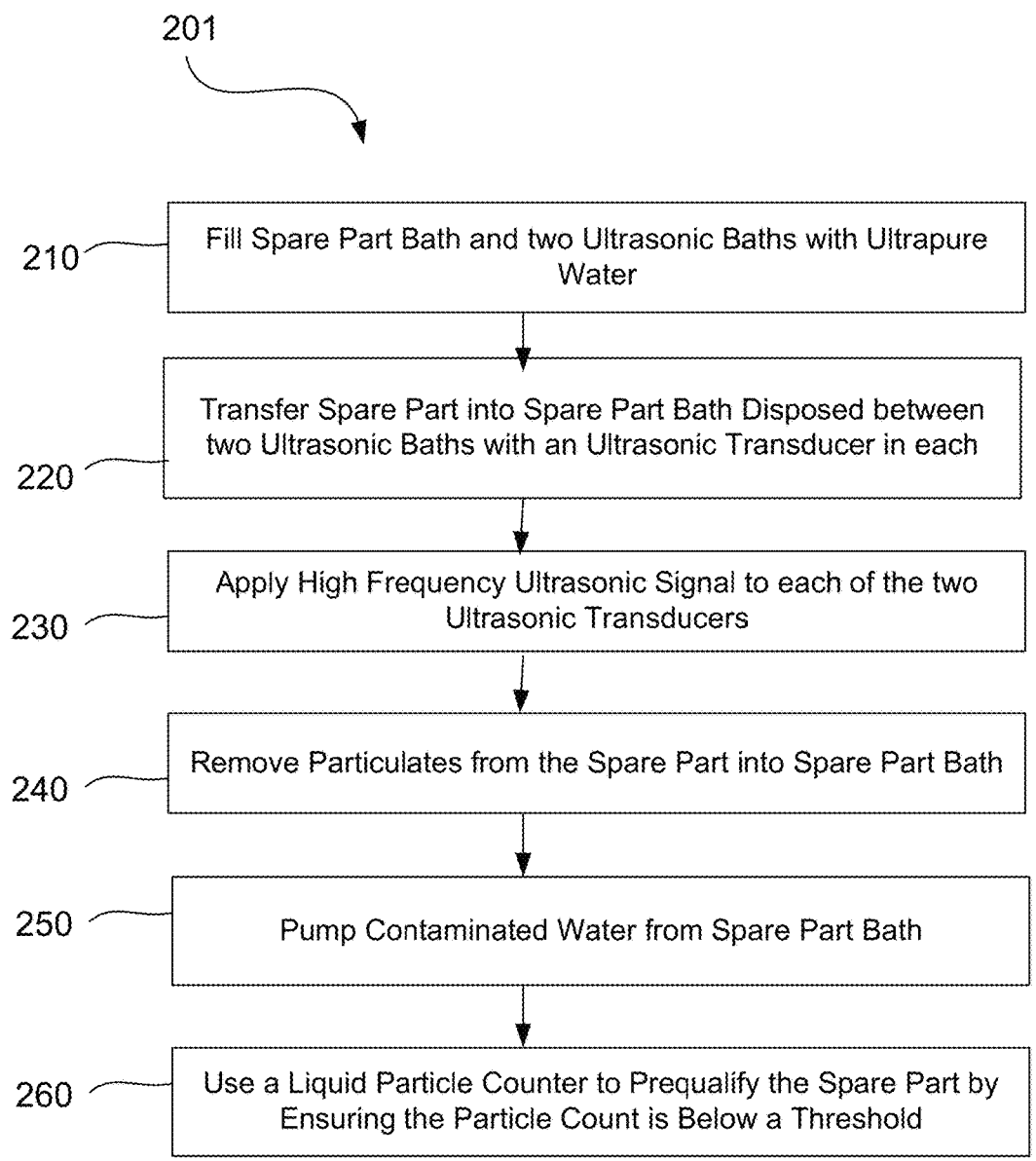
FIG. 2 shows a method for cleaning and sampling components for a substrate processing chamber according to embodiments.

FIG. 2 shows a method for cleaning and sampling components 201 for a substrate processing chamber according to embodiments. The sampling bath 101 is filled with ultrapure water in operation 210. Filling the sampling bath involves filling cleaning tub 113b and ultrasonic tubs 115b with the ultrapure water. Spare part 105 is transferred into cleaning bath where it is supported by spare part support 110 (operation 220). An RF signal of 80 kHz is applied to two ultrasonic transducers disposed in two ultrasonic baths 115a disposed on either side of cleaning bath 113a in operation 230. The immersion of spare part 105 in ultrapure water in combination with the cavitation caused by the excitation of the ultrasonic transducers dislodges particulates from spare part 105 (operation 240). The dislodged particulates diffuse into cleaning bath 113a. The dislodged particulates in combination with the ultrapure water may be referred to as contaminated water herein. The contaminated water is pumped from cleaning bath 113a (operation 250) and diluted with additional ultrapure water in selectable and predictable proportions. The quantity of particulates in the contaminated water is measured in a liquid particle counter 130 in operation 260. Once the quantity of particulates in the contaminated water falls below a selectable threshold, the cleaning process may be terminated and spare part 105 may be removed from cleaning bath 113a and cleaning tub 113b.

Figure 3:
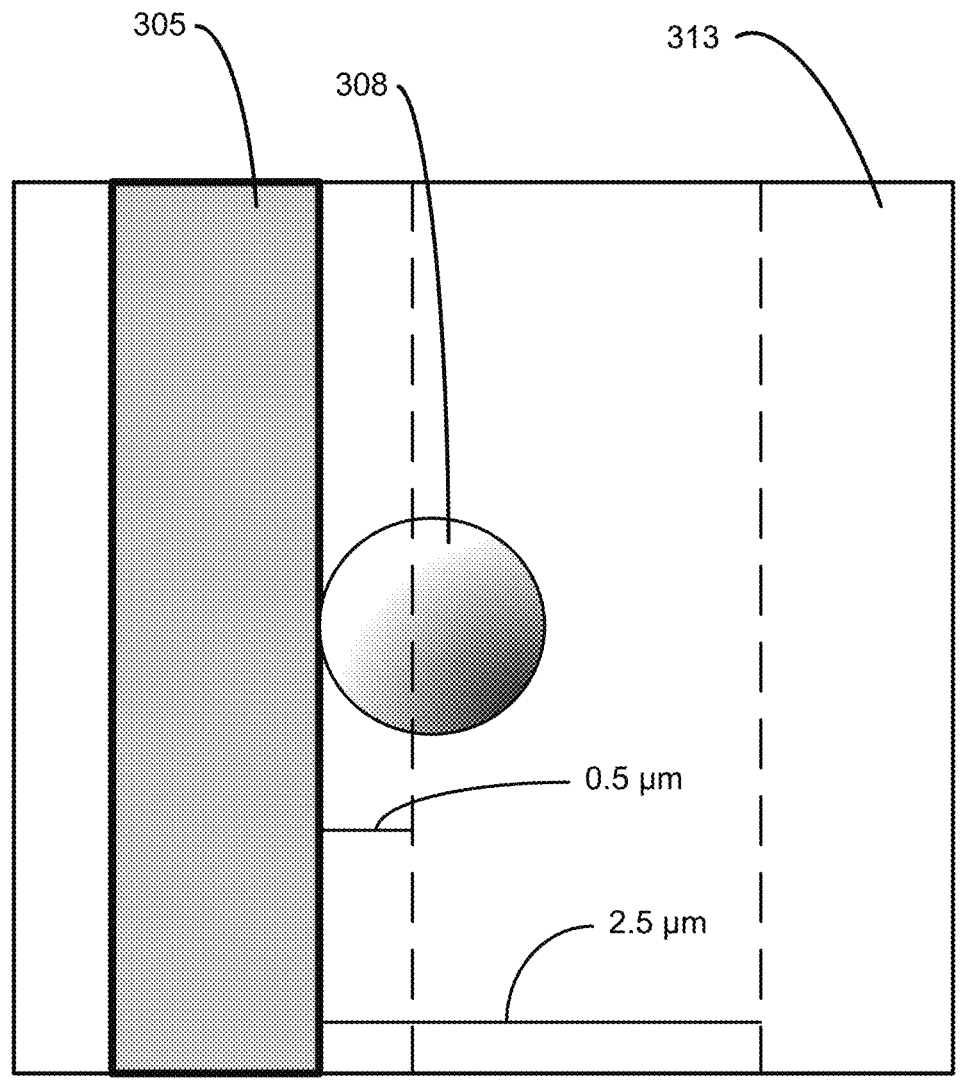
FIG. 3 shows a close-up view of a system for cleaning and sampling components for a substrate processing chamber according to embodiments.

FIG. 3 shows a close-up view of a system for cleaning and sampling components for a substrate processing chamber according to embodiments. FIG. 3 is a close-up of a cleaning event inside cleaning bath 113a. A spare part portion 305 of spare part 105 is shown with an attached particle 308 which is to be removed using ultrasonic agitation. Typical ultrasonic frequencies lie in the 20 kHz to 40 kHz range and may result in a large boundary layer (e.g. 2.5 μm) compared to current "killer" particle sizes which negatively impact semiconductor device yield. The sizes of killer particles becomes smaller and smaller as semiconductor linewidths are reduced. Using ultrasonic frequencies in the range from 50 kHz to 300 kHz (e.g. 80 kHz) reduces the boundary layer thickness (e.g. 0.5 μm in the figure) which facilitates the disturbance of particle 308 by the ultrasonic energy. The boundary layer remains more stationary compared to regions outside the boundary layer since the mass transport in the layer is dominated by the stationary surface of spare part portion 305. The reduced thickness of the boundary layer enables particle 308 to become dislodged and flow away from the surface into cleaning bath portion 313 and later pass sampling pump 120 before being analyzed in liquid particle counter 130.

Process flows may ordinarily involve cleaning and checking the cleanliness of spare in separate equipment and even separate facilities which reduces the sampling frequency and increases costs. Implementing the hardware and processes described herein offers the benefit of reducing costs, increasing the number of (e.g. spare) parts sampled, and increasing process simplicity afforded by cleaning and quantifying defectivity in the same equipment or in the same vessel in embodiments. The sampling bath may be installed at the manufacturing plant, an intermediate facility or at the destination semiconductor manufacturing site to increase flexibility. A benefit of the simplified process flow includes a reduction of the opportunity of introducing contamination to the part to-be-cleaned during handling and transportation stages. A further benefit of the processes and hardware described herein include in-process monitoring which allows the end-point of the cleaning process to be determined as the spare part is cleaned.

During the cleaning processes described herein, cleaning bath 113a may be at a temperature between 10° C. and 90° C., between 20° C. and 80° C., or between 25° C. and 50° C. according to embodiments. Ultrasonic baths (115a) may be at the same temperature as cleaning bath 113a in embodiments. Ultrasonic baths (115a) may be at an ultrasonic bath temperature between 10° C. and 90° C., between 20° C. and 80° C. or between 25 and 50° C., according to embodiments. Cleaning bath 113a may be at a temperature greater than 15° C., greater than 20° C., greater than 25° C., or greater than 30° C. in embodiments. Higher temperatures for cleaning bath 113a have been found to correlate with a greater removal efficiency of particulates from spare part 105 according to embodiments. Ultrasonic baths 115a may be at a temperature greater than 15° C., greater than 20° C., greater than 25° C., or greater than 30° C. in embodiments. The temperature will rise simply by the introduction of cavitational energy to the cleaning bath 113a and ultrasonic baths 115a. A resistive heater may not be included or may be included according to embodiments to achieve higher temperatures of the baths. Cleaning bath 113a and ultrasonic baths 115a may comprise mostly the same or the same type of fluid and may comprise mostly water or water of a variety of purities according to embodiments.

Figure 4:
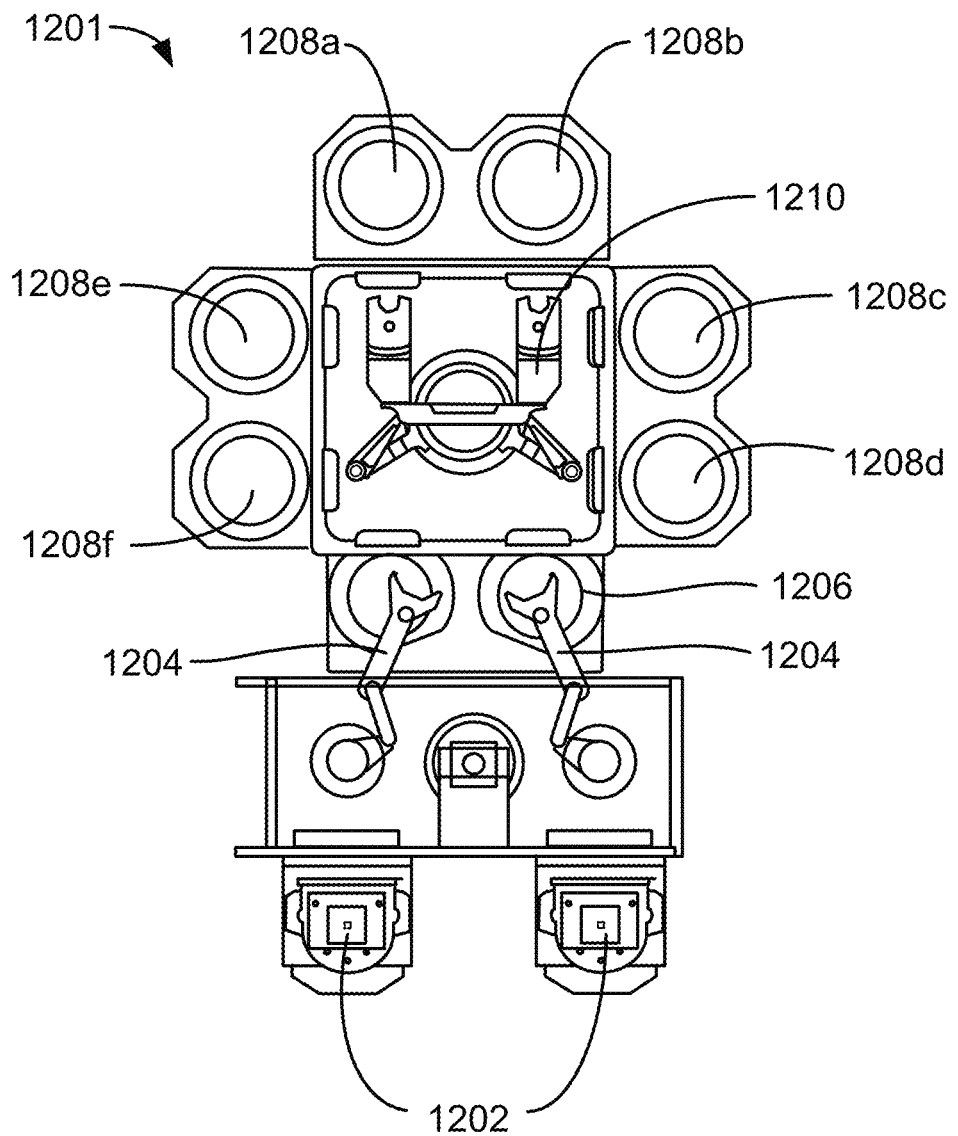
FIG. 4 shows a top view of an exemplary substrate processing system according to embodiments.

FIG. 4 shows a substrate processing system 1201 of deposition, etching, baking, and curing chambers. Each chamber may contain components and spare parts which can be cleaned using the systems described herein, according to embodiments. In the figure, a pair of front opening unified pods (load lock chambers 1202) supply substrates of a variety of sizes that are received by robotic arms 1204 and placed into a low pressure holding area 1206 before being placed into one of the substrate processing chambers 1208a-f. A second robotic arm 1210 may be used to transport the substrate wafers from the holding area 1206 to the substrate processing chambers 1208a-f and back. Each substrate processing chamber 1208a-f, can be outfitted to perform a number of substrate processing operations including the dry etch processes described herein in addition to cyclical layer deposition (CLD), atomic layer deposition (ALD), chemical vapor deposition (CVD), physical vapor deposition (PVD), etch, pre-clean, degas, orientation, and other substrate processes.

As used herein "substrate" may be a support substrate with or without layers formed thereon. The patterned substrate may be an insulator or a semiconductor of a variety of doping concentrations and profiles and may, for example, be a semiconductor substrate of the type used in the manufacture of integrated circuits.

Having disclosed several embodiments, it will be recognized by those of skill in the art that various modifications, alternative constructions, and equivalents may be used without departing from the spirit of the disclosed embodiments. Additionally, a number of well-known processes and elements have not been described to avoid unnecessarily obscuring the present embodiments. Accordingly, the above description should not be taken as limiting the scope of the claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the claims, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the dielectric material" includes reference to one or more dielectric materials and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

The invention claimed is:

1. An ultrasonic cleaning and sampling system, comprising:
   a cleaning tub including a cleaning bath;
   a first ultrasonic tub and a second ultrasonic tub, wherein the first ultrasonic tub is disposed on the opposite side of the cleaning tub from the second ultrasonic tub;
   a first impermeable barrier disposed between the first ultrasonic tub and the cleaning tub, wherein the first impermeable barrier passes ultrasonic energy from the first ultrasonic tub into the cleaning tub when each of the first ultrasonic tub and the cleaning tub are filled with water;
   a second impermeable barrier disposed between the second ultrasonic tub and the cleaning tub, wherein the second impermeable barrier passes ultrasonic energy from the second ultrasonic tub into the cleaning tub when each of the second ultrasonic tub and the cleaning tub are filled with water;
   a first ultrasonic transducer and a second ultrasonic transducer, wherein the first ultrasonic transducer is in a first ultrasonic bath and the second ultrasonic transducer is in a second ultrasonic bath, wherein the first and second ultrasonic baths are each separately enclosed such that liquid, ions, or particulates do not flow in or out from the first and second ultrasonic baths to the cleaning bath;
   an ultrapure water source delivers ultrapure water into the cleaning bath;
   a sampling pump fluidly coupled to the cleaning bath and removes contaminated water from the cleaning bath;
   a liquid particle counter fluidly coupled to a dilution unit and measures the particle concentration of the contaminated water using optical scattering;
   a recirculation pump fluidly coupled to the cleaning bath;
   a large particle filter fluidly coupled to the recirculation pump; and
   a small particle filter fluidly coupled to the large particle filter, wherein a recirculation path connects to the cleaning bath at an outlet and an inlet and the recirculation path comprises the recirculation pump, the large particle filter and the small particle filter.

2. The ultrasonic cleaning and sampling system of claim 1 wherein the first ultrasonic transducer is configured to be driven at a first frequency which is greater than 20 kHz to produce cavitation in the cleaning tub.

3. The ultrasonic cleaning and sampling system of claim 1 wherein the first ultrasonic transducer and the second ultrasonic transducer are configured to be driven at a same frequency to concurrently produce cavitation in the cleaning tub.

4. The ultrasonic cleaning and sampling system of claim 1 wherein the first ultrasonic transducer is configured to be driven at a first megasonic frequency to produce cavitation in the cleaning tub.

5. The ultrasonic cleaning and sampling system of claim 1 wherein a recirculation pumping speed of the recirculation pump is between 10 liters/min and 200 liters/min.

6. The ultrasonic cleaning and sampling system of claim 1 wherein the first ultrasonic tub is configured such that the first ultrasonic transducer is submersible.

7. The ultrasonic cleaning and sampling system of claim 1 wherein the small particle filter is selected to remove particles larger than 10 nm while passing particles smaller than 10 nm.

8. The ultrasonic cleaning and sampling system of claim 1 wherein the large particle filter is selected to remove particles larger than 30 nm while passing particles smaller than 30 nm.

9. The ultrasonic cleaning and sampling system of claim 1 wherein the recirculation path further comprises an ion-exchange filter.

* * * * *